United States Patent [19]

von Kleinsorgen

[11] Patent Number: 4,714,085
[45] Date of Patent: Dec. 22, 1987

[54] COSMETIC STICK FOR A POWDER PENCIL

[75] Inventor: Reinhard von Kleinsorgen, Nuremberg, Fed. Rep. of Germany

[73] Assignee: Schwan-Stabilo Schwanhäusser GmbH & Co., Fed. Rep. of Germany

[21] Appl. No.: 545,633

[22] Filed: Oct. 26, 1983

[30] Foreign Application Priority Data

May 6, 1983 [DE] Fed. Rep. of Germany ... 8313487[U]

[51] Int. Cl.$^4$ .................. A45D 40/20; A61K 7/02
[52] U.S. Cl. .................. 132/88.7; 132/79 C; 132/DIG. 3; 401/49; 401/96; 424/63
[58] Field of Search .......... 132/1 R, 9, 88.7, DIG. 3, 132/79 R, 79 C; 401/49, 96; 424/63

[56] References Cited

U.S. PATENT DOCUMENTS

| | | | |
|---|---|---|---|
| 292,650 | 1/1884 | Hecklinger | 401/96 X |
| 1,075,880 | 10/1913 | Walls | 401/49 X |
| 1,576,567 | 3/1926 | Buhl-Bonanno | 132/88.7 X |
| 2,566,722 | 9/1951 | Friedberg | 132/88.7 |
| 3,192,933 | 7/1965 | Prince | 132/88.7 |
| 3,957,066 | 5/1976 | Dahm | 132/88.7 |
| 4,413,921 | 11/1983 | Fotiu et al. | 401/49 X |

FOREIGN PATENT DOCUMENTS 309482 11/1929 United Kingdom .................. 401/96

Primary Examiner—Robert P. Swiatek
Assistant Examiner—Carolyn A. Harrison

[57] ABSTRACT

A cosmetic stick for a powder pencil for directly applying powder to the skin comprises a stable stick body formed from bound base powder components, pigment and, optionally, a binding agent and adhesion agent. The stick body is formed from at least two stick body portions which are joined together over the length of the stick and which differ in composition from each other.

12 Claims, 2 Drawing Figures

COSMETIC STICK FOR A POWDER PENCIL

BACKGROUND OF THE INVENTION

The present invention relates generally to a cosmetic stick for a powder stick or pencil for directly applying powder to the skin.

A cosmetic stick for a powder pencil for directly applying powder to the skin comprises for example base components in powder form, which are bound together to form a rigid or stable stick body, together with pigments and possibly a binding agent and adhesion-enhancing agent. Such powder sticks or pencils which are used for decorative cosmetic purposes differ from powder compacts or powder blocks insofar as a powder stick or pencil is used to apply the powder directly to the ski by rubbing the actual powder pencil against the surface of the skin, whereas the application of powder from a powder compact or a powder block requires an applicator or powder puff, by means of which powder is first picked up on the applicator from the solid block of powder and then transferred from the applicator on to the skin. A considerable advantage of powder pencils of that kind is that the powder material can be applied to the skin in a substantially more accurate and more finely controlled manner, and in the form of finer and more delicate patterns as may be required, than is possible when using an applicator. Consequently, powder pencils are suitable in particular for eye make-up.

In order to ensure that the surface of the powder pencil or the stick body therein does not pick up moisture and grease from the skin by virtue of the direct contact therewith, which would result in the surface of the powder pencil becoming clogged in a relatively short time, being a phenomenon which may be referred to as glazing, thereby preventing further powder from being transferred from the stick body portion of the powder pencil on to the skin, a particular material may be added to the cosmetic stick, in addition to the above-mentioned base components, the particles of the additional particulate material being harder than the base components and being in the range of from 10 to 100$\mu$ in size (see for example German patent specification No. 3 103 128). The base components may also partially or predominantly comprise flake-like particles, comprising for example mica (see for example German patent specification No. 2 540 877).

When using powders for decorative cosmetic purposes, it is the usual and a desirable practice to provide a plurality of colour tones or shades so that transitional areas and shading areas can be shaded away or toned down. For that purpose, in the context of conventional powder compacts and powder blocks, it is known for a plurality of powder colours or shades which are matched to each other to be disposed in a packaging unit. When the person using the powder wishes to have a shading effect or a gradual and progressive variation in powder colouring, then the applicator is used to apply powder material from powder blocks or compacts of differet colours, to the skin. When carrying out such a make-up operation, it is essentially a matter of the skill of the person using the powder to obtain correct matching of the powder colours applied, by applying suitable amounts of the respective powders to the skin by means of the applicator. It will be appreciated however that not every person using the powder make up of that kind may have such a high level of skill and the effects are not always satisfactory. When using powder pencils or sticks, a corresponding procedure for applying different shades of powders can be performed only by using a plurality of powder pencils in succession to apply different powder shades to the skin. That mode of procedure also requires considerable skill if a satisfactory shading effect is to be produced, while it is also necessary to buy and carry around, a number of different powder pencils for giving the different powder colours.

SUMMARY OF THE INVENTION

An object of the present invention is to provide a cosmetic stick member for a powder stick or pencil, which makes it possible to produce colour shadow effects, shading effects and colour changes or transitions.

Another object of the present invention is to provide a cosmetic stick member which permits greater versatility in the application of powder directly to the skin of a person.

Yet another object of the present invention is to provide a cosmetic or powder stick for the direct application of powder to the skin, which permits the tone or shade of powder actually applied to be varied by the person using the powder stick, with only a relatively low level of skill in applying same.

These and other objects are achieved by a cosmetic stick member for a powder stick or pencil, for directly applying powder to the skin, comprising a stable or rigid stick body which is formed from bound base powder components, pigment and optionally binding agent and adhesion-enhancing agent, wherein the stick body is formed from at least two stick body portions which are joined together over the length of the stick and which are of different compositions from each other.

Therefore, in the cosmetic stick in accordance with the present invention, the stick cross-section, over the entire length thereof, is made up of powder material of different compositions. The difference in composition is primarily that the powder materials contain different pigments. It should be appreciated however that the invention is not restricted to that aspect, for it is also possible for the cosmetic stick to contain components which, when they come together on the skin and thereby mix together, produce an increased binding effect or the like. In accordance with the principles of the present invention, the stick body comprises at least two stick body portions which are of different compositions, but it is also possible for the stick body to comprise three or four or even more stick body portions of different compositions. Because the stick body portions extend over the length of the stick and are joined together, it is possible to apply powder material of just a single composition to the skin, by rubbing the appropriate stick body portion thereagainst, thus applying just a single powder colour, in the same way as using a conventional powder pencil. In addition however, and it will be appreciated that this is one of the advantages of the present invention, it is possible to apply a mixture of the different powder materials directly to the skin by rubbing against the skin a region of the end of the powder pencil which embraces or includes the line of separation between the plurality of body stick portions which are joined together over the length of the stick to make up the stick body itself. When the powder pencil with such a stick body configuration is used in that way, the powder actually applied to the skin will be made up of two or possibly more different powders which thus mix together on the skin, to provide the desired powder effect. The shading for example of the powder applied to the skin can be the subject of fine adjustment or 'colour tuning', by the powder pencil being slightly turned about its longitudinal axis towards one side of the above-mentioned separating line or the other, with the result that the area of one of the stick body portions which is operatively involved in applying powder to the skin is increased, on one side of the separating line, while the area of the stick body portion on the other side of the separating line is correspondingly reduced, thereby altering the colour balance between the two powders being applied to the skin. In that way, by suitably adjusting the powder pencil relative to the skin, the person using the powder pencil can directly check, right at the beginning of the powder-application process, whether the colouring effect actually being produced is the desired effect. In addition, as the powder-application procedure progresses, the colouring or shading produced by the application of the powder can be intensified or weakened, by slightly rotating the powder pencil in the appropriate direction.

It has been found that this possibility of precise adjustment and shading is based on a mixing effect in respect of the individual powder materials of the stick body portions, such effect occurring directly as the powders are applied to the skin. In other words, the powder materials of the respective stick body portions are mixed together at the moment at which the powder pencil or cosmetic stick forming the powder pencil is rubbed against the skin, thereby providing for stripe-free colour shading, unlike for example colour pencils in which the stick material is a solid, fatty or wax-like material and in which the different colour tones or shades are essentially formed by layers of the different colouring materials being laid down one upon the other.

In an advantageous aspect of the present invention, the stick body portions are of a prismatic shape and are joined together, at least substantially parallel to the longitudinal axis of the stick body. When the stick body comprises only two stick body portions which differ from each other, the line of separation between those two stick body portions extends in a straight line through the centre of the stick body, which is generally circular. On the other hand, when the stick body is made up of a larger number of stick body portions, the stick body portions are in the form of circular sectors, in cross-section thereof, assuming that, as is usual, the stick is of a cylindrical configuration. It should be appreciated however that other forms of stick body portions and separating line configurations are also possible, for example the separating line between the stick body portions may extend in a helical configuration about the longitudinal axis of the stick body.

DESCRIPTION OF THE PREFERRED EMBODIMENT

Figure 1:
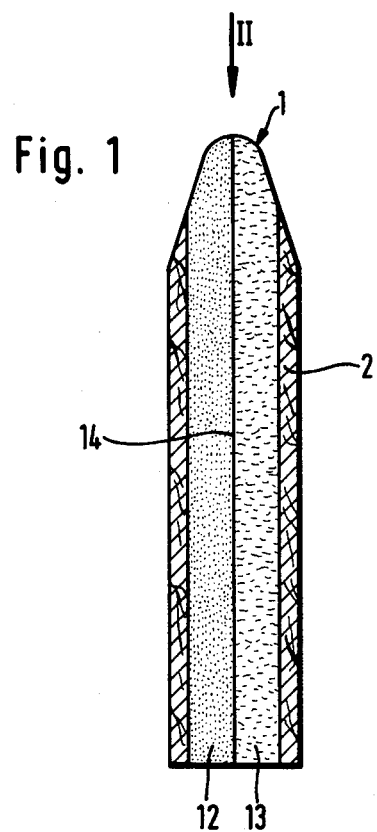
FIG. 1 shows a view in axial section of a powder pencil including an embodiment of a cosmetic stick in accordance with the principles of the present invention.
Figure 2:
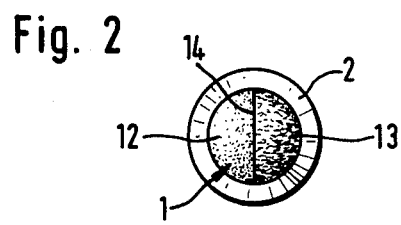
FIG. 2 shows a view of the powder pencil shown in FIG. 1, viewing in the direction indicated by the arrow II in FIG. 1.

Referring firstly to FIG. 1, shown therein is a powder pencil which comprises a cosmetic stick 1 and a sheath or shank portion 2 which encases the stick 1 and which comprises a material which can be sharpened substantially to a point, for example wood or a plastic material. The stick body 1 within the sheath 2 is substantially in the form of an elongate cylinder of round cross-section, and is made up of a plurality of stick body portions 12 and 13. In the illustrated embodiment, there are two such stick body portions 12 and 13 which are therefore each of a semicircular configuration in cross-section, as can be clearly seen from FIG. 2. The stick body portions 12 and 13 are fixedly joined together over the length of the stick body, along a contact surface as indicated at 14, which coincides with the longitudinal central plane of the stick body 1. It will be appreciated that the stick body 1 may be made up of a larger number of stick body portions of suitable prismatic shape which are suitably joined together, for example parallel to the longitudinal axis of the stick body.

The two stick body portions 12 and 13 differ in regard to their structure and composition, insofar as at least the colouring pigments used in the two or more stick body portions are different. It will be noted that the stick body portions comprise powder base material, pigment and optionally a binding agent and an adhesion-enhancing agent, which are thus bound together to form the stable or substantially rigid stick body. The stick body portions may additionally include a particulate material comprising particles which are of greater hardness than the other stick body components and which are for example of a particle size of between 10 and $100\mu$. A preferred particle size of the particulate material is from 20 to $50\mu$, with the particles being of an irregular configuration. The particles of the powder base material may predominantly be of a flake-like configuration, and the stick body may be of a porous structure.

Where the stick body portions contain different colouring pigments, the choice of colouring pigments is such as to provide two powder colours or shades which are suitably matched to each other, which the man skilled in the cosmetics art can readily ascertain. The differences in composition of the body portions 12 and 13 are indicated in the drawing, by the dot-like and the short line illustration respectively thereof.

It will be appreciated that the above-described embodiment is described by way of example and illustration of the present invention, and that various modifications and alterations may be made therein without thereby departing from the spirit and scope of the present invention.

What is claimed is:

1. A cosmetic stick for an elongate powder pencil for directly applying powder to the skin, having a stable stick body comprising powder base material, pigment and, optionally, a binding agent and an adhesion-enhancing agent, wherein the stick body is formed from at least two elongate stick portions which are joined together over their length and of which one portion contains a pigment or pigments differing in color from the pigment or pigments contained in the other portion, and wherein said portion, in addition to said powder base material, pigment and, optionally, said binding agent and said adhesion-enhancing agent, contains particulate material comprising particles which are of greater hardness than the particles of said powder base material and which are of a particle size of between 10 and $100\mu$.

2. A stick as set forth in claim 1 wherein said stick portions are of a prismatic shape and are joined together at least substantially parallel to the longitudinal axis of the stick body.

3. A stick as set forth in claim 1 wherein said particles of said particulate material have a particle size of from 20 to 50$\mu$ and are of an irregular configuration.

4. A stick as set forth in claim 1 wherein the powder base material comprises particles which are predominantly of a flake-like configuration.

5. A stick as set forth in claim 1 which is of a porous structure.

6. In a powder pencil having a stick body comprising a powder material and a pigment, bound together to form an elongate stable stick body, the improvement that provides that the stick body is made up of a plurality of elongate stick body portions each of which has a cross-section smaller than the cross-section of the stick body and which are joined together over at least substantially the whole length of the stick body, the stick body portions being of different compositions from each other and each composition comprising at least a powder base material and a pigment bound together to form a stable stick body portion and, in addition, a particulate material comprising particles which are of greater hardness than the particles of said powder base material and which are of a particle size of between 10 and 100$\mu$.

7. A powder pencil as set forth in claim 6 and further including a binding agent.

8. A powder pencil as set forth in claim 6 and further including an adhesion-enhancing agent.

9. A powder pencil as set forth in claim 6 wherein each said stick body portion is of an at least substantially uniform cross-section over the length thereof.

10. A powder pencil as set forth in claim 9 wherein said stick body portions are joined together at least substantially parallel to the longitudinal axis of the stick body.

11. A powder pencil as set forth in claim 6 wherein said compositions of said respective stick body portions differ from each other in respect of at least said pigment.

12. A powder pencil as set forth in claim 6 and further comprising a sheathing member encasing said stick body.

* * * * *